(12) United States Patent
Dave et al.

(10) Patent No.: US 8,876,860 B2
(45) Date of Patent: Nov. 4, 2014

(54) VASCULAR CLOSURE DEVICE

(75) Inventors: Vipul Bhupendra Dave, Hillsborough, NJ (US); Chao-Chin Chen, Edison, NJ (US); Thomas Palermo, San Jose, CA (US)

(73) Assignee: Cordis Corporation, Fremont, CA (US)

( * ) Notice: Subject to any disclaimer, the term of this patent is extended or adjusted under 35 U.S.C. 154(b) by 621 days.

(21) Appl. No.: 12/405,087

(22) Filed: Mar. 16, 2009

(65) Prior Publication Data

US 2009/0318955 A1    Dec. 24, 2009

Related U.S. Application Data

(60) Provisional application No. 61/036,772, filed on Mar. 14, 2008.

(51) Int. Cl.
*A61B 17/08* (2006.01)

(52) U.S. Cl.
USPC .................. 606/213; 424/422; 424/423

(58) Field of Classification Search
USPC .............. 424/422–428, 443, 444; 606/213; 623/23.72, 23.73, 23.75, 23.76
See application file for complete search history.

(56) References Cited

U.S. PATENT DOCUMENTS

| | | | |
|---|---|---|---|
| 5,043,216 A * | 8/1991 | Misoo et al. | 428/397 |
| 5,108,421 A | 4/1992 | Fowler | |
| 5,326,350 A * | 7/1994 | Li | 623/23.72 |
| 6,325,789 B1 * | 12/2001 | Janzen et al. | 604/506 |
| 2003/0106163 A1 * | 6/2003 | Neogi et al. | 8/116.1 |
| 2004/0203146 A1 * | 10/2004 | Gazit et al. | 435/399 |
| 2005/0058692 A1 * | 3/2005 | Hai-Quan et al. | 424/443 |
| 2005/0085854 A1 | 4/2005 | Ginn | |
| 2005/0085856 A1 | 4/2005 | Ginn | |
| 2005/0267528 A1 | 12/2005 | Ginn et al. | |
| 2006/0212127 A1 * | 9/2006 | Karabey et al. | 623/23.75 |
| 2007/0027553 A1 * | 2/2007 | Biran et al. | 623/23.74 |

FOREIGN PATENT DOCUMENTS

| | | |
|---|---|---|
| EP | 1234587 B1 | 2/2001 |
| WO | 00/21470 A1 | 4/2000 |
| WO | WO 02/074192 * | 9/2002 |
| WO | WO 02/074192 A2 | 9/2002 |
| WO | WO 2007/044510 * | 4/2007 |
| WO | WO 2007/044510 A1 | 4/2007 |

OTHER PUBLICATIONS

Bikales, Norbert M., Nonwoven Fabrics, Encyclopedia of Polymer Science and Engineering, 1987, pp. 204-253, vol. 10.
Chatterjee, Pronoy K., Absorbency, Textile Science and Technology 7, 1985, pp. 67-68, vol. 7.
European Examination Report mailed on Mar. 7, 2012 from corresponding European Patent Application No. 09719811.3.

* cited by examiner

*Primary Examiner* — Dianne Dornbusch

(57) ABSTRACT

The present invention provides a porous structure that works very effectively to seal a puncture site with optimum porosity, absorbent capacity and perfect anatomical fit. The plug density and other fiber properties/geometry (total denier; number of filaments; etc) have provided an efficient structure that allows instantaneous absorption of blood during deployment. The final size of the plug with absorbed fluids provides an anatomical fit and seals the puncture site within few minutes after deployment.

7 Claims, 15 Drawing Sheets

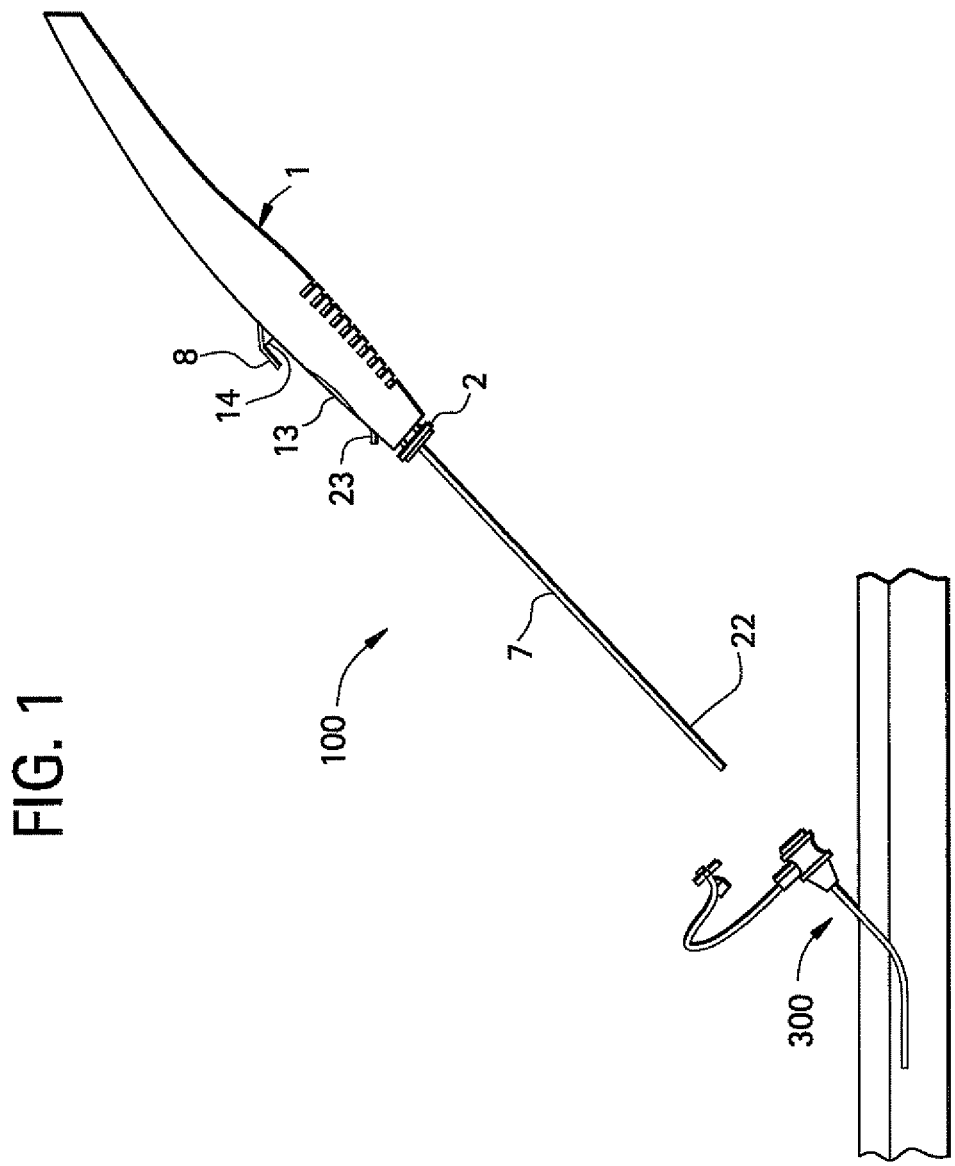

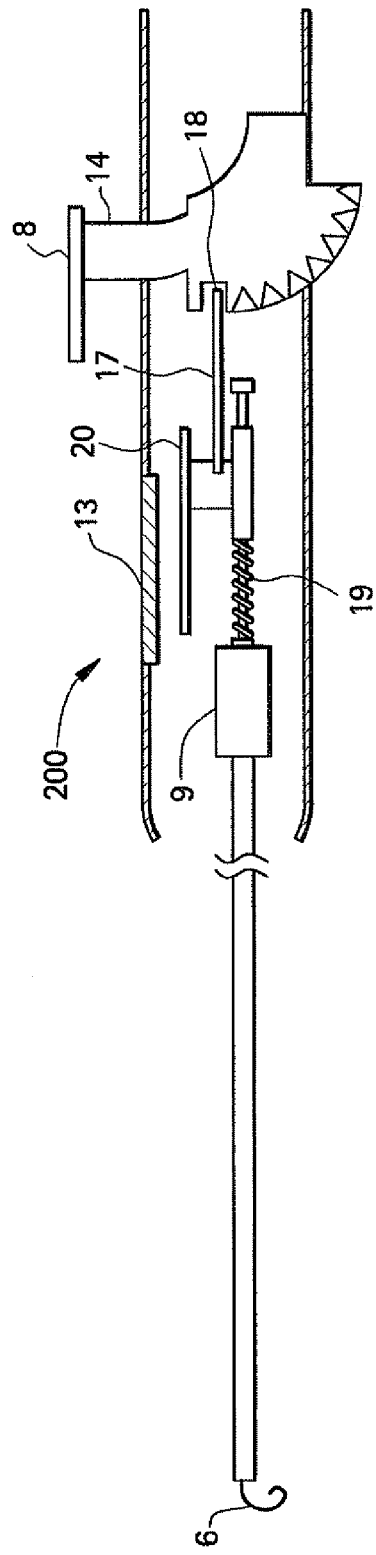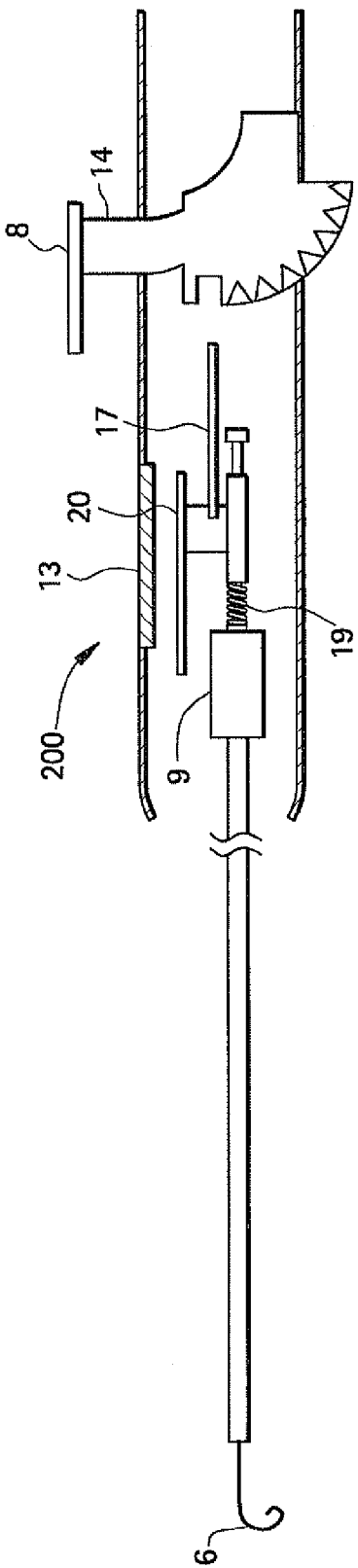

Plug

100μm

VASCULAR CLOSURE DEVICE

RELATED APPLICATIONS

This application claims the benefit of U.S. Provisional Application Ser. No. 61/036,772 filed on Mar. 14, 2008, the disclosure of which is incorporated in its entirety herein.

FIELD OF THE INVENTION

The present invention relates generally to apparatus and methods for sealing or closing passages through tissue, and more particularly to devices for sealing punctures or other openings communicating with body lumens, such as blood vessels.

BACKGROUND OF THE INVENTION

Catheterization and interventional procedures, such as angioplasty and stenting, generally are performed by inserting a hollow needle through a patient's skin and muscle tissue into the vascular system. This creates a puncture wound in a blood vessel, frequently the femoral artery, which, once the interventional procedure has been completed, needs to be closed or sealed in a suitable manner.

Procedures and devices have been proposed for accomplishing such closure which involve the use of an introducer sheath that is placed in the tract of the puncture wound following which a closure delivering device is introduced through the introducer sheath to deploy a sealing element within the tract. An indicator wire may be used to locate the edge of the tract. After the closure delivery device deploys the sealing element, the indicator wire and the device are retracted. Examples of such procedures and devices are disclosed in application Ser. No. 10/687,848, filed Oct. 17, 2003 and Ser. No. 10/850,795 filed May 21, 2004. In these procedures and devices, it would be desirable to exploit features of the patient's anatomy to optimize sealing of the puncture wound.

SUMMARY OF THE INVENTION

The present invention provides a porous structure that works very effectively to seal a puncture site with optimum porosity, absorbent capacity and perfect anatomical fit. The plug density and other fiber properties/geometry (total denier; number of filaments; etc) have provided an efficient structure that allows instantaneous absorption of blood during deployment. The final size of the plug with absorbed fluids provides an anatomical fit and seals the puncture site within few minutes after deployment. These plug characteristics have provided superior clinical performance compared to current competitive products. This invention provides less plug material to absorb more blood compared to other plug type of technologies.

In one aspect of the invention, the sealing element comprises a porous fibrous structure configured for sealing a wound. The fibrous structure is formed from at least one randomly oriented fiber. The randomly oriented fiber includes at least one polymer with a porosity ranging from 65 to 98%.

In another aspect of the invention, the sealing element comprises a porous fibrous structure configured for sealing a wound. The fibrous structure is formed from at least one randomly oriented fiber. The randomly oriented fiber includes at least one polymer with an absorbent capacity ranging from 2.5 g/g to 4.0 g/g.

In another aspect of the invention, the sealing element comprises a porous fibrous structure configured for sealing a wound. The fibrous structure is formed from at least one randomly oriented fiber. The randomly oriented fiber includes at least one polymer with a density ranging from 0.05 to 5 g/cc.

In another aspect of the invention, the sealing element comprises a porous fibrous structure configured for sealing a wound. The fibrous structure is formed from at least one randomly oriented fiber. The randomly oriented fiber includes at least one polymer with an absorption time varying from 30 to 90 days.

In one aspect of the invention, the sealing element is positioned between the tissue membrane and the wall of the artery lumen when the membrane engages the sealing element. Alternatively, the sealing element partially protrudes from the tissue membrane when the membrane engages the sealing element.

Preferably, the membrane retains the sealing element at a desired position adjacent the wall of the lumen. Also preferably, the tissue membrane urges the sealing element against the wall of the lumen.

DESCRIPTION OF THE DRAWINGS

In order to better appreciate how the above recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1 illustrates a side-view of a sealing element deployment device in accordance with a preferred embodiment of the present invention.

FIGS. 4(a-b) illustrate a distal portion of the device in accordance with a preferred embodiment of the present invention.

DETAILED DESCRIPTION OF THE INVENTION

Figure 2A:
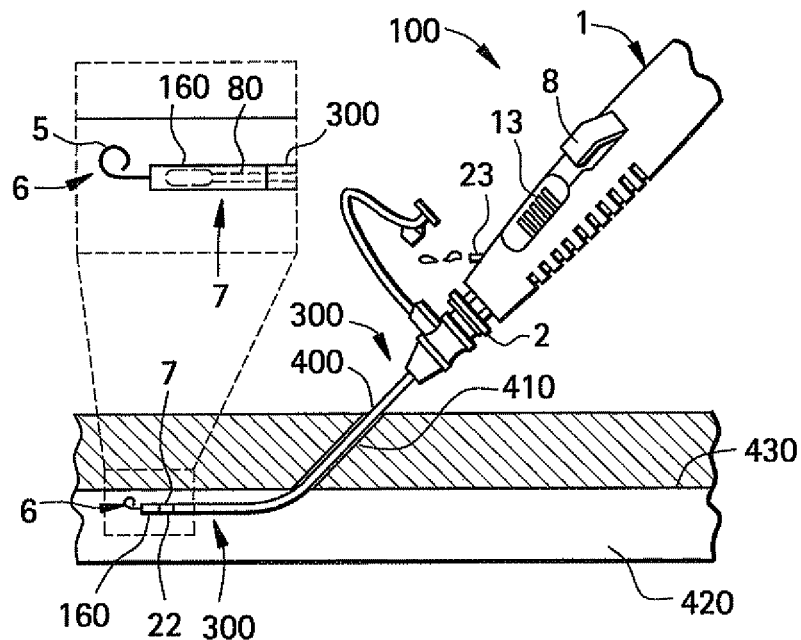
FIG. 2A illustrates a side-view of a sealing element deployment device in accordance with a preferred embodiment of the present invention.

A device 100 for deploying a detachable sealing element 160 (shown in FIG. 2) in a puncture wound is shown in FIG. 1, herein referred to as a closure device 100. Examples of such a sealing element or plug 160 are described in U.S. application Ser. No. 10/687,848. filed Oct. 17, 2003. Ser. No. 10/850, 795 filed May 21, 2004. and Ser. No. 11/038,995. filed Jan. 19, 2005. each of which applications are hereby incorporated by reference. Sealing element 160 occludes blood flow from a puncture. In a preferred embodiment, the sealing element 160 will be fabricated from a material that may expand upon contact with blood, such as a felt made from polyglycolic acid and/or polylactic acid polymers or copolymers or other materials such as collagens. The sealing element 160 may also have one or more hemostasis, antibiotic or other therapeutic agents added to it.

Alternatively, in other preferred embodiments, the sealing element 160 will be made in such a manner that it will expand spontaneously or upon removal of a restraining force. In still other embodiments, the sealing element 160 can be expandable mechanically, hydraulically or pneumatically. In all such embodiments, it is preferred that the sealing element 160 be fabricated from a bioabsorbable material.

It is generally known to use multilayered fabrics in connection with medical procedures. For example, multilayered fabrics are used as all purpose pads, wound dressings, surgical meshes, including hernia repair meshes, adhesion prevention meshes and tissue reinforcement meshes, defect closure devices, and hemostats. Additionally, multilayered fabrics are useful for tissue engineering and orthopedic applications. The recent emergence of tissue engineering offers numerous approaches to repair and regenerate damaged/diseased tissue. Tissue engineering strategies have explored the use of biomaterials that ultimately can restore or improve tissue function. The use of colonizable and remodelable scaffolding materials has been studied extensively as tissue templates, conduits, barriers and reservoirs. In particular, synthetic and natural materials in the form of foams, sponges, gels, hydrogels, textiles, and nonwovens have been used in vitro and in vivo to reconstruct/regenerate biological tissue, as well as deliver agents for inducing tissue growth. The different forms of scaffolds may be laminated to form a multilayered tissue-engineering scaffold.

As used herein, the term "nonwoven fabric" includes, but is not limited to, bonded fabrics, formed fabrics, or engineered fabrics, that are manufactured by processes other than spinning, weaving or knitting. More specifically, the term "nonwoven fabric" refers to a porous, textile-like material, usually in flat sheet form, composed primarily or entirely of staple fibers assembled in a web, sheet or bats. The structure of the nonwoven fabric is based on the arrangement of, for example, staple fibers that are typically arranged more or less randomly. The tensile stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include spinning, weaving or knitting.

Preferably, the nonwoven fabric is made by processes other than spinning, weaving or knitting. For example, the nonwoven fabric may be prepared from yarn, scrims, netting or filaments that have been made by processes that include spinning, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be between about 0.1 and 3.0 inches long, preferably between about 0.75 and 2.5 inches, and most preferably between about 1.5 and 2.0 inches. The staple may be carded to create a nonwoven bat, which may be then needle-punched or calendared into an absorbable nonwoven fabric. Additionally, the staple may be kinked or piled.

Figure 12A:
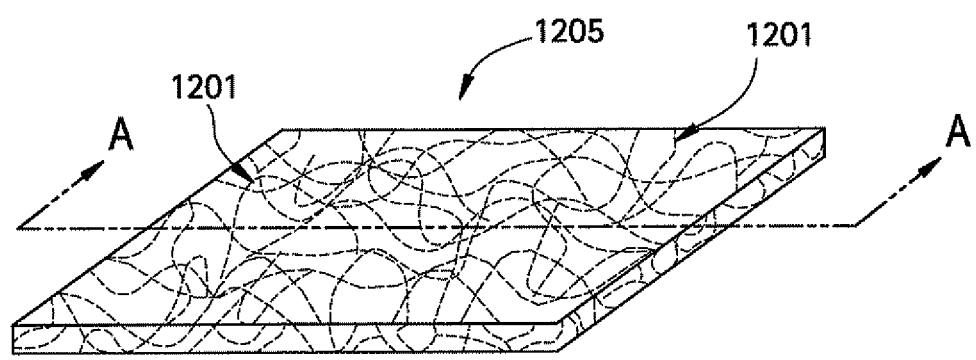
FIG. 12A is a schematic representation of a non-woven fibrous mat according to one embodiment of the present invention.
Figure 12B:
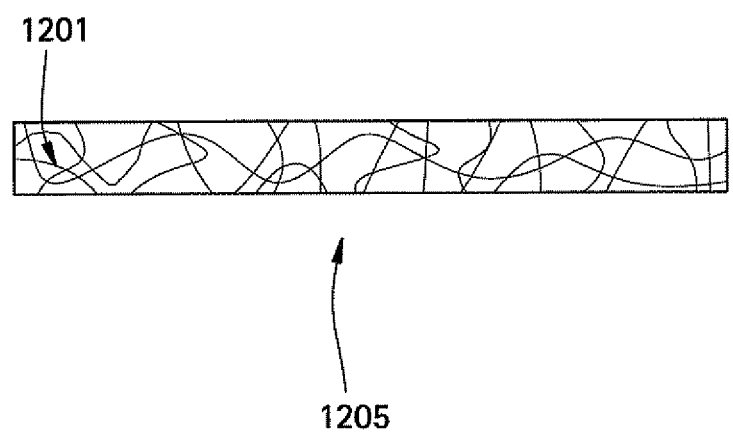
FIG. 12B is a section view of the non-woven fibrous mat depicted in FIG. 12A taken along reference line A-A.

FIGS. 12A and 12B are schematic representations of a non-woven fibrous mat according to one embodiment of the present invention. The non-woven mat 1205 is formed from filaments or fibers 1201 entangled in random order.

Other methods known for the production of nonwoven fabrics may be utilized and include such processes as air laying, wet forming and stitch bonding. Such procedures are generally discussed in the Encyclopedia of Polymer Science and Engineering, Vol. 10, pp. 204-253 (1987) and Introduction to Nonwovens by Albin Turbak (Tappi Press, Atlanta Ga. 1999), both incorporated herein in their entirety by reference.

The thickness of the nonwoven fabric may range from about 0.25 to 2 mm. The basis weight of the nonwoven fabric ranges from about 0.01 to 0.2 g/in2; preferably from about 0.03 to 0.1 g/in2; and most preferably from about 0.04 to 0.08 g/in2.

Additionally, the nonwoven fabric may comprise pharmacologically and biologically active agents, including but not limited to, wound healing agents, antibacterial agents, antimicrobial agents, growth factors, analgesic and anesthetic agents. When used as a tissue scaffold, the reinforced absorbable multilayer fabric may be seeded or cultured with appropriate cell types prior to implantation for the targeted tissue.

The vascular plug of the current invention is a novel extra-vascular closure device with a unique visually guided deployment mechanism that delivers a polyglycolic acid (PGA) plug atop the femoral artery anchored by the neuro-vascular bundle sheath.

A presently preferred embodiment employs needle-weaved polyglycolic acid (PGA) fibers that degrade through chemical hydrolysis, within 60 to 90 days, of unstable bonds in the crystalline phase to lactic acid and glycolic acid, followed by enzymatic attack and participation in the Kreb's cycle to metabolize to carbon dioxide and water. In one embodiment, sealing element 160 exhibits modest expansion in the range of approximately 0-15%.

A typical process to make the vascular closure plug according to one embodiment of the present invention follows. The desired absorbable polymer resin [e.g., poly (glycolic acid)] is melt extruded in to multi-filaments (about 40 to 70 filaments) with different denier (about 120 to 150 denier) and tenacity (about 3 to 7 grams/denier). During the melt spinning process, a spin finish is applied on the fiber surface to prevent excessive fiber breakage. The fibers are then crimped and cut in to short staple fibers (for example, 1-2 inches staple lengths), carded and needle punched to prepare a non-woven mat with the desired density and integrity. The mat is rinsed (scoured) with a solvent (e.g., isopropanol or acetone or hexane, ethyl acetate or other co-solvents) to remove the spin finish and dried; and then cut in to cylindrical plugs or other desired geometry.

Inherent viscosity (IV) of pre-sterile PGA plugs ranged from about 0.8 to 1.0 dL/g as determined by Ubbelohde viscometer in hexafluroisopropanol (HFIP), and the weight average molecular weight (Mw) was determined to be 24,000 to 27,000 g/mole as determined by tetradetection gel permeation chromatography (GPC-T, Model 302) by Viscotek using (HFIP) as the mobile phase. The melting point of the plug was about 235° C. with the heat of fusion value of about 86 J/g. The percent crystallinity of PGA was determined to be about 62% based on heat of fusion value of 139 J/g for pure PGA.

Figure 13:
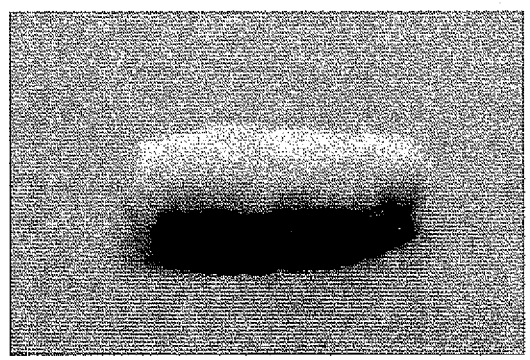
FIG. 13 is an optical view of a typical PGA plug according to one embodiment of the present invention.
Figure 14:
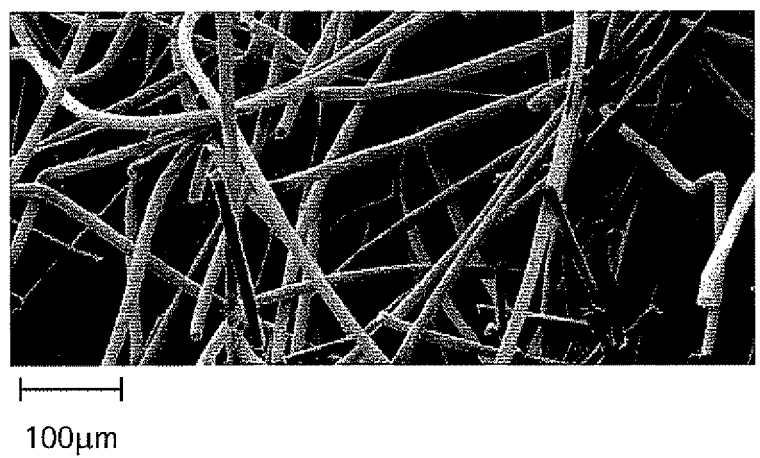
FIG. 14 is a scanning electron micrograph view of a typical PGA plug according to one embodiment of the present invention.

An optical and a scanning electron micrograph of a typical PGA plug are shown in FIGS. 13 and 14 respectively.

The PGA plug is prepared from a nonwoven fibrous structure as shown in FIG. 14. The plug structure can have different porosity and absorbent capacity based on the density of the non-woven structure. The porosity was optimized in order to provide rapid hemostasis. The porous structure will have different porosity and absorbent capacity based on the density of the structure. The description of pore structure, absorbent capacity, mechanism of liquid flow and structure property relationships are generally discussed in the Textile Science and Technology Series (Elsevier), Volume 7 on Absorbency, 1985 (Edited by P. K. Chatterjee), Chapter II incorporated herein in their entirety by reference.

Porosity: For example, mass of each 6 F plug is about 10 mgs. Dimensions of the uncompressed and compressed 6 F plug are 5 mm or 0.196 inches (diameter) and 10 mm or 0.393 inches long; and 1.85 mm or 0.073 inches (diameter) and 7.23 mm or 0.284 inches long, respectively. Based on these dimensions, the density of the uncompressed and compressed plug is 0.05 g/cc and 0.5 g/cc, respectively. Density of the PGA fiber is about 1.6 g/cc. Porosity is calculated by:

$$\text{Porosity} = 1 - \text{Density (Felt)}/\text{Density (fiber)}$$

$$\text{Porosity (Uncompressed Plug)} = 1 - 0.05/1.6 = 1 - 0.03125 = 0.9687 \text{ or } 96.87\%$$

$$\text{Porosity (Compressed Plug)} = 1 - 0.5/1.6 = 1 - 0.3125 = 0.6875 \text{ or } 68.75\%$$

The plug is deployed in the compressed state and gradually reaches the uncompressed state. So porosity of the plug varies from 68% to 97%.

Figure 15:
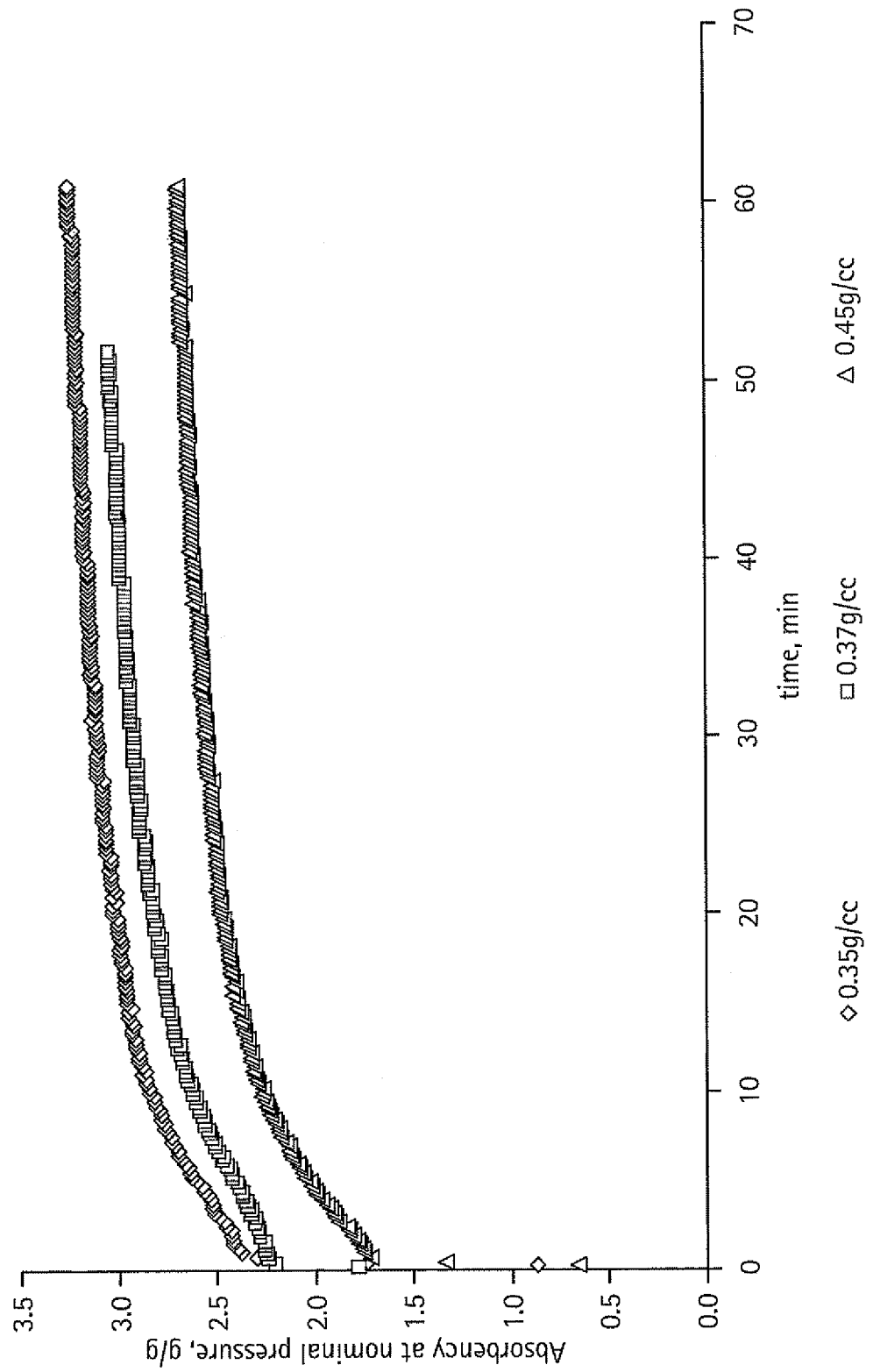
FIG. 15 is a graph showing the absorbent capacity of a nonwoven PGA felt at different densities.

Absorbent Capacity: This is a material property and is independent of geometry. This property can be measured for a flat geometry (disc) with different densities using a method called Gravimetric Absorbency Test (GAT). Basic principles of this method have been described in pages 67-68 in the above-mentioned reference. Briefly, the amount of liquid absorbed in the structure is continuously measured gravimetrically by an electronic balance as a function of time and the data is collected via a computer. This method is very sensitive as it has the ability to record infinitesimal changes in absorption of liquid. FIG. 15 shows the absorbent capacity of the nonwoven PGA felt at different densities. The material exhibits high absorbency rate during the first minute and then slowly and continuously picks up fluid over time. At nominal (low) pressure, absorbency increases at lower densities. The absorbent capacity ranges from about 2.75 g/g to 3.3 g/g for densities ranging from 0.35 g/cc to 0.45 g/cc. The density of the plug in the compressed state is about 0.5 g/cc, so the absorbent capacity of the plug is about 2.75 g/g and gradually increases as the density of plug decreases. The capacity will change with different hydrostatic pressure. PGA plug absorbency works mainly due to the physical porosity and not from material affinity for blood or moisture. The plug can also be prepared from other fibers that are more hydrophilic (e.g., oxidized regenerated cellulose, ORC) in order to provide higher absorbent capacity and thereby can reduce the plug weight. The plug can also be prepared from other porous structures (foams; etc) that can provide the same clinical performance. The plug can also be used for other applications to seal a puncture site.

In Vitro Absorption Characteristics: The method used for the wetting characteristics follow. The plug while it is in the tip of the delivery shaft is soaked in heparinized porcine (with a 1:100 heparin blood ratio, with 1 ml=100 units of heparin) for 2 minutes. Then the deployment force is measured (about 1.5 pounds) and the length, diameter, and weight measurements are collected. The deployed plug is then soaked again for 2 minutes in heparinized blood, and the length, diameter, and weight measurements are again taken for a second time after the soak. The table below summarizes these measurements on devices that were sterilized by e-beam and aged for about 50 days at 55° C. and 17% RH.

The results show that there was an instantaneous weight gain of the plugs in the first two minutes plugs as the weight increased from 10 mgs to about 33 mgs. Further weight gain was observed after additional 2 minutes of soaking time as the weight increased from about 33 mgs to 39 mgs. The weight gain was the highest in the first two minutes as was observed in the GAT measurements, and then was a gradual weight gain as a function of time. Diameter of the compressed plugs also increased from 0.073 inches to 0.076 inches, and the length increased from 0.284 inches to 0.38 inches. Change in diameter and length of the plug was not significant with additional 2 minutes of soaking time. These results show that the plugs are functional after accelerated aggressive aging conditions.

Figure 16:
FIG. 16 is a cross-sectional view of a plug deployed in the porcine vessel.

In Vivo Anatomical Characteristics: FIG. 16 shows the cross-section of the plug deployed in the porcine vessel, and sectioned within 1 h of deployment. The image looks like an ellipsoid. Volume ($4/3 \times 22/7 \times r1 \times r2 \times r3$) of an ellipsoid was calculated by measuring the dimensions of the plug from the histo image:

r1=1.81 mm; r2=1.81 mm; r3=3.61 mm

Based on this, volume of the expanded plug is about 49.55 cubic mm. The volume of the compressed unexpanded plug (cylinder) is 19.44 cubic mm (density of the compressed unexpanded plug is 0.5 g/cc). So, there is about 145% increase in volume of the plug upon expansion in the body. This corresponds well with the in vitro testing result of instantaneous absorption and expansion of the plug at the puncture site. It should also be noted that there is almost a perfect anatomical fit of the plug to provide a seal at the puncture site.

The present invention provides a porous structure that works very effectively to seal a puncture site with optimum porosity, absorbent capacity and perfect anatomical fit. The plug density and other fiber properties/geometry (total denier; number of filaments; etc) have provided an efficient structure that allows instantaneous absorption of blood during deployment. The final size of the plug with absorbed fluids provides an anatomical fit and seals the puncture site within few minutes after deployment. These plug characteristics have provided superior clinical performance compared to current competitive products. This invention provides less plug material to absorb more blood compared to other plug type of technologies.

Figure 19:
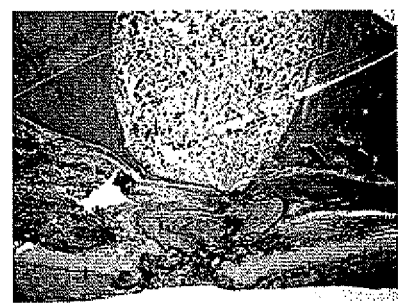
FIG. 19 is a cross-sectional view of a plug deployed in the porcine vessel.
Figure 17:
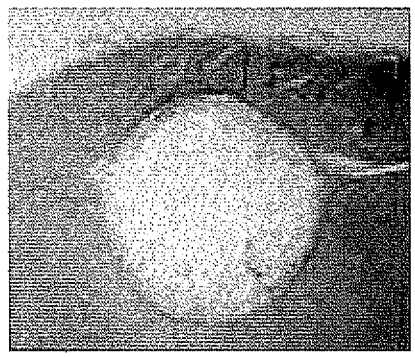
FIG. 17 is a cross-sectional view of a plug after 3 days in a rat gluteal flap model.
Figure 18:
FIG. 18 is a cross-sectional view of a plug after 90 days in a rat gluteal flap model.

Several studies were conducted to understand the biocompatibility and absorption of the plugs in different animal models. The evaluation of the tissue reaction and absorption of the plug was determined in a rat gluteal flap model and porcine vessels. The results FIGS. 17 and 18 show the cross-sections of the plug after 3 days and 90 days, respectively, in a rat gluteal flap model. It shows significant mass loss at 90-day time point with minimum tissue reactions. FIGS. 16 and 19 represents the cross-sections of the plug deployed in the porcine vessel, and sectioned within 1 h of deployment. FIG. 16 shows that the plug is secured beneath the femoral sheath fascia layer after device deployment. The fascia layer provides support to the plug for secured positioning and holds the plug in place. FIG. 19 shows that the plug is positioned above arteriotomy at the outer margin of the vessel wall. It should be noted that the plug absorbs blood in a very short time and a perfect anatomical fit of the plug is obtained to seal the puncture site.

The ECLIPSE clinical trial has been conducted in the U.S. at multiple centers comparing the safety and efficacy of the plug and manual compression (MC) in femoral access site closure with 2:1 randomization in patients following 6 Fr diagnostic and interventional coronary and peripheral procedures. Both reduced time to hemostasis (TTH) and time to ambulation (TTA) were significantly reduced in patients with plug compared with MC. Plug deployment was achieved in about 1 minute on average following procedure. Remarkably, there were no 30-day access site complications reported in either treatment cohort.

The closure device 100 for deploying the sealing element 160 includes a tubular elongate member 1, herein referred to as the "housing," which houses various components that will be described below. The device 100 also comprises a wire actuator 2 that is external and distal to the housing 1 and is slidably mounted and configured to actuate an indicator wire 6, as described below. Extending through the distal end of the housing 1 is a deployment tube 7 configured to be received by an introducer sheath 300 known in the art. The deployment tube 7 is slightly longer than the introducer sheath 300. The deployment tube 7 receives an indicator wire 6 (shown in FIGS. 2a and 2b) and a plunger 80, which operates as a backing member supporting a detachable sealing element 160 at a distal section of the deployment tube 7. The plunger 80 preferably includes a channel through which the indicator wire 6 may be received within the tube 7. The channel is preferably located on or near the edge or the periphery of the backing portion of the plunger 80, i.e., near the internal surface of the deployment tube 7. Optionally, an indicator wire tube or other lumen (not shown) may be provided within the interior of the deployment tube 7. The indicator wire tube is preferably attached to the housing 1 at its proximal end, and extends through the deployment tube 7. The indicator wire 6 then extends through the indicator wire tube or other lumen and exits the indicator wire tube at or near the distal end of the deployment tube 7. (Additional details of the structure and operation of the plunger 80 are described in Ser. No. 10/850, 795. filed May 21, 2004. which is incorporated by reference.)

The deployment tube 7 includes an inlet port 22 in the distal section of the tube 7, configured to take in blood when exposed to a vessel, and the housing 1 includes an outlet port 23 communicatively coupled to the inlet port 22 for allowing the blood to exit outside of the puncture wound. Also extending out of the housing is a trigger 8 that preferably includes a rotary link 14 configured to deploy the detachable sealing element 160. Before operation of the closure device 100, the rotary link 14 is locked, i.e., the operator is prevented from actuating the rotary link 14 despite pressing the trigger 8, as described below.

Turning to FIGS. 2(A-D), deployment of a detachable sealing element 160 within a puncture wound 400 using the closure device 100 is illustrated. An introducer sheath 300 is already deployed within the tract 410 of the wound 400 with its distal end 310 exposed within the lumen 420 of a blood vessel defined by a vessel wall 430. The deployment tube 7 of the closure device 100 is inserted into the introducer sheath 300. Upon substantially complete insertion, the device 100 is engaged with the introducer sheath 300, and the distal section of the deployment tube 7 extends out of the distal end of the sheath 300. When the inlet port 22 is exposed to the lumen 420 of the vessel 430, blood will enter the inlet port 22 and travel out of the outlet port 23 extending out of the housing 1. The blood exiting the outlet port 23 will be visible to the operator (not shown) of the device 100, notifying the operator that the distal end of the deployment tube 7 is within the lumen 420 of the vessel 430 and outside of the tract 410 of the puncture wound 400.

Also, upon substantially complete insertion, the wire actuator 2 of the device 100 is actuated by the proximal end of the sheath 300, causing the wire actuator 2 to be pushed toward the housing 1. The wire actuator 2 is mechanically coupled to the indicator wire 6 and configured to actuate the indicator wire 6 in the distal direction. Thus, as the wire actuator 2 is pushed towards the housing 1, the wire actuator 2 causes the indicator wire 6 to extend out of the distal end of the deployment tube 7. When the indicator wire 6 exits the tube 7, the distal section of the wire 6 forms into a loop 5 located adjacent the distal tip of the tube 7. The loop 5 of the wire 6 will come into contact with the vessel wall 430 near the edge 415 of the tract 410 when the device 100 and the sheath 300 are withdrawn, as shown in FIG. 2b.

Figure 2B:
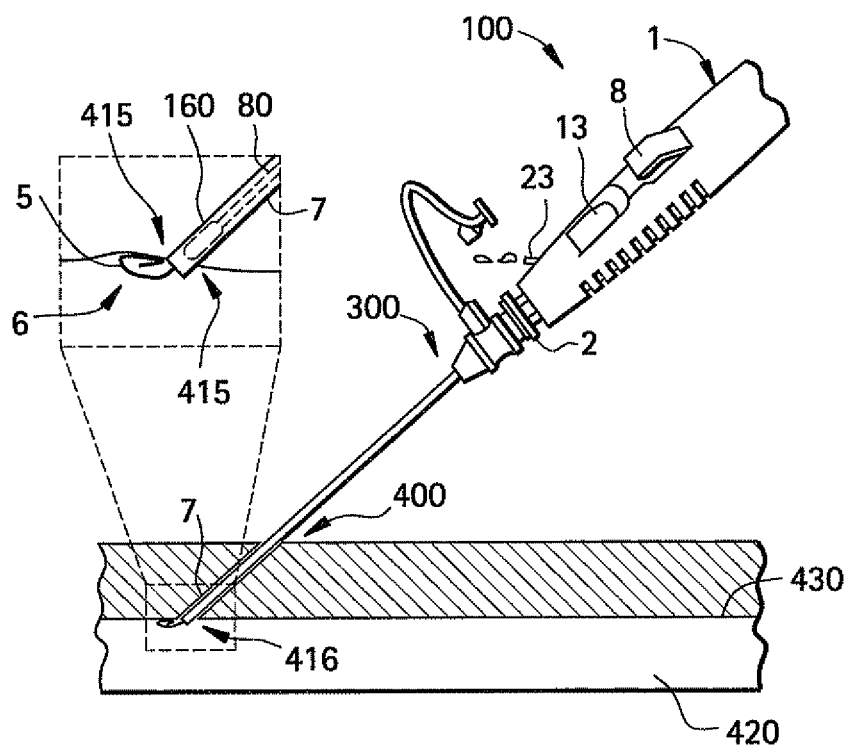
FIG. 2B illustrates a side-view of a sealing element deployment device in accordance with a preferred embodiment of the present invention.

Turning to FIG. 2b. after the device 100 is inserted and engaged into the sheath 300 as described above, the operator withdraws or pulls back the device 100 and sheath 300 within the tract 410. When the distal section of the deployment tube 7 exits the lumen 420 and enters the tract 410, the inlet port 22 is no longer exposed to the blood within the lumen 420 and thus, the blood flow out of the outlet port 23 ceases. This notifies the operator that the distal section of the deployment tube 7 has exited the lumen 420 and entered the tract 410 of the puncture wound 400. The indicator wire's 6 resistance that is caused by the loop 5 engaging the vessel wall 430 will unlock the rotary link 14, as described below, and optionally toggle the indicator window 13 to a state that indicates that the loop 5 has engaged the vessel wall 430 near the edge 415 of the tract 410, which places the distal end of the deployment tube 7 at a desirable location within the tract 410 and substantially adjacent to the edge 415. In the embodiment shown in FIG. 2b. the indicator window 13 toggles from a striped pattern, FIG. 2a. to a solid pattern, as described below.

Figure 2C:
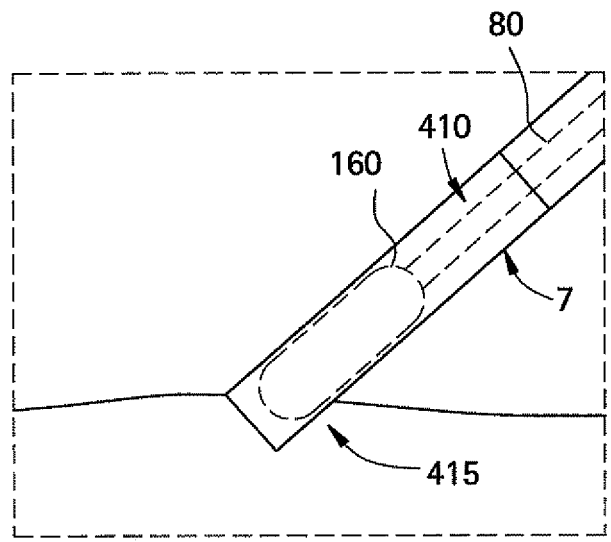
FIG. 2C illustrates a side-view of a distal portion of the sealing element deployment device in accordance with a preferred embodiment of the present invention.
Figure 2D:
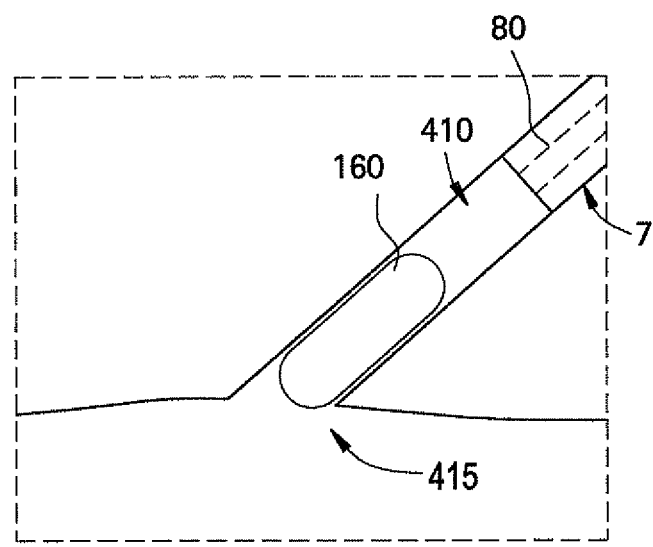
FIG. 2D illustrates a side-view of a distal portion of the sealing element deployment device in accordance with a preferred embodiment of the present invention.

The operator is then enabled to actuate the unlocked rotary link 14 to deploy the sealing element 160 by pressing the trigger 8. Turning to FIGS. 2C and 2D, the rotary link 14 actuates and withdraws both the wire 6 and the tube 7 while the sealing element 160 remains substantially in place by the pusher 80, thereby deploying the sealing element 160. The device 100 then disengages from the sealing element 160, thus sealing or plugging the puncture wound 400. Preferably, in one motion, the rotary link 14 is configured to withdraw the indicator wire 6 into the tube 7 before the tube 7 is withdrawn. Thus, the wire 6 is withdrawn before the sealing element 160 deployed, preventing the wire 6 from interfering with the deployment of the sealing element 160, such as damaging or dislodging the sealing element 160.

Figure 3:
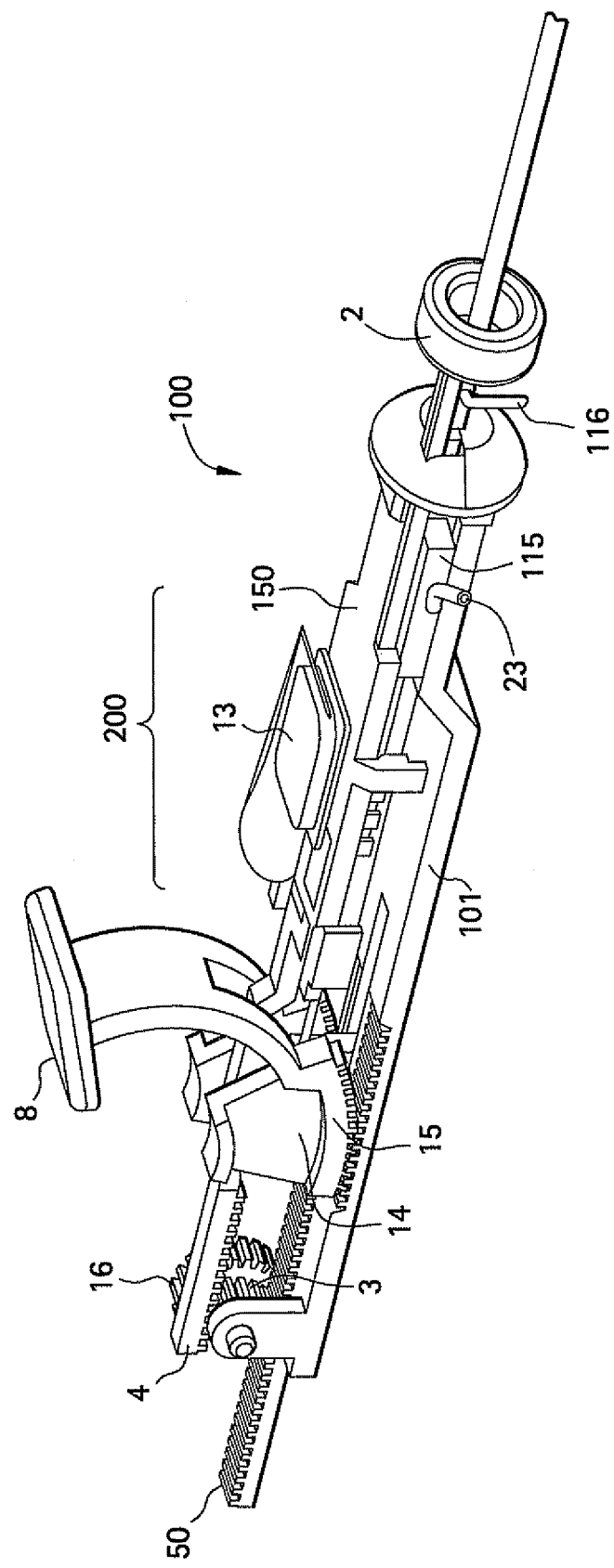
FIG. 3 illustrates a perspective view of components of a sealing element deployment device in accordance with a preferred embodiment of the present invention.

Turning to FIG. 3, a rack and pinion system for actuating the tube 7 and the wire 6 within the housing 1 of the device 100 is shown. The device 100 is shown not engaged to an introducer sheath 300, and thus the wire actuator 2 is in its original state away from the housing 1. The wire actuator 2 is coupled to a first rack 4 that is configured to engage a first gear 3 when the wire actuator 2 is actuated in the proximal direction as described above. The first gear 3 is attached to a second gear 16, which causes a second rack 50 to move in the distal direction. The second rack 50 is engaged with the indicator wire 6, causing the indicator wire 6 to extend out of the tube 7 when wire actuator 2 is actuated by engaging with the introducer sheath 300 as described above. The wire actuator 2 proximally withdraws the first rack 4, which rotates the second gear 16 via the first gear 3, which then advances distally the second rack 50, thus advancing distally the indicator wire 6, causing the indicator wire to extend out of the deployment tube 7.

The first and second gears 3 and 16 share an axis that is secured by a bottom plate 101. The bottom plate 101 is actuated by a trigger that includes a rotary link 14. When the trigger 8 is pressed to deploy the plug 160, the rotary link 14, which includes an arcuate gear section 15 that engages and actuates the bottom plate 101 in the proximal direction, is actuated. A tube collar 115, which is engaged to the deployment tube 7, is anchored at a distal portion of the bottom plate 101. When the bottom plate 101 is withdrawn proximally, the collar tube 115 is withdrawn as well, which in turn withdraws proximally the deployment tube 7, which deploys the plug 160. Proximally withdrawing the bottom plate 101 causes the first gear 3 to rotate along the first rack 4, which is locked in place by the wire actuator 2 engaged with the introducer sheath 300. Proximal to the wire actuator 2 is a post 116 that extends from the housing 1. When the distal portion of the closure device 100 is inserted into the lumen of the introducer sheath 300, a proximal portion of the introducer sheath 300 that defines a lip (not shown) engages the post 116, which connects and locks the closure device 100 to the introducer sheath 300. Thus, the second rack 50 is proximally withdrawn by the second gear 16, which causes the indicator wire 6 to retract substantially simultaneously with the deployment tube 7. The figures show that the first gear 3 has a smaller diameter than the second gear 16. First and second gears 3 and 16 each provide a mechanical advantage to the control of the indicator wire 6 and deployment tube 7 respectively. Preferably, the mechanical advantage regarding the indicator wire 6 is 4:1 and the mechanical advantage regarding the deployment tube 7 is 2:1. Other mechanical advantage relationships may be used e.g., 3:1 for the indicator wire 6 and 1.5:1 for the tube 7. It is preferred that the mechanical advantage for the indicator wire 6 be twice that for the tube 7. Thus, when trigger 8 is depressed, the bottom plate 101 and tube collar 115 will withdraw the tube 7 more slowly than the indicator wire 6 is withdrawn into the device 100 and the indicator wire 6 will be retracted into the deployment tube 7 before the sealing element 160 is deployed and/or disengaged from the tube 7 and the device 100. As described above, this advantageously prevents the indicator wire 6 from interfering with the deployment of the sealing element 160.

One of ordinary skill in the art will appreciate that though a rack and pinion system is described and shown in FIG. 3, any suitable type of actuating system may be configured to retract the indicator wire 6 before a sealing element 160 is deployed and/or disengaged from the device 100 in accordance with a preferred embodiment of the present invention. For example, a hydraulic, electronic, and/or a pulley system may be used instead of or in addition to the rack and pinion system to retract the indicator wire 6 into the deployment tube 7 before the sealing element 160 is deployed and/or disengaged from the device 100.

The housing 1 can also include an indicator assembly 200 coupled to a stationary top plate 150 of the device 100. The indicator assembly 200 can indicate to the operator, via an indicator panel 13 in the top plate 150, whether the distal end of the deployment tube 7 is in the desired location, e.g., near the edge 415 of the tract 410 of the puncture wound. In addition to, or in the alternative, the indicator assembly 200 may further lock the trigger 8 until the deployment tube 7 is in the desired location. In FIGS. 4A and 4B, an implementation of the indicator assembly 200 of the device 100 is shown. The indicator assembly 200 comprises an indicator 20, indicator spring 19 and lockout plate 17. As can be seen from FIG. 4A, a slidable lockout plate 17 engages groove 18 in rotary link 14, thereby preventing substantial movement of rotary link 14. The indicator spring 19 applies a proximal force on the lockout plate 17 to maintain the lockout plate's 17 position even after the indicator wire 6 is deployed from the tube 7.

Turning to FIG. 4B, the indicator wire 6 is fixedly attached to the lockout plate 17, which is coupled to a block 9 via the indicator spring 19. The block 9 is in a secured position, fixed to the housing 1 and/or the tube 7. Because the indicator wire 6 is connected to the tube 7 and/or housing 1 via a spring 19 and slidable lockout plate 17, the indicator wire 6 is capable of axial movement independent of the housing 1 and/or tube 7.

During operation, after the indicator wire 6 has been deployed through the puncture wound 400 with the formed loop 5 exposed to the lumen 420 of a vessel defined by a vessel wall 430, the operator is then ready to withdraw the device 100 and sheath 300 to deploy the sealing element 160 within the tract 410 of the puncture wound 400. Even if blood stops flowing out of the outlet port 23, that only indicates that the inlet port 22 is within the tract 410, not necessarily that the sealing element 160 is desirably near the edge 415 of the tract 410. However, the indicator wire 6 may provide such an indication. When the loop 5 of the wire 6 approaches the edge 415 of the tract 410, the loop 5 will engage the vessel wall 430 near the edge 415 as the device 100 is withdrawn by the operator. When the loop 5 engages the vessel wall 430, it will cause a force to be applied on the wire 6 toward the distal direction, or direction opposite that of the device 100 as its being withdrawn. This force will overcome the force of the spring 19 securing the lockout plate 17, proximally withdraw the lockout plate 17 in the distal direction, and cause the lockout plate 17 to disengage from the groove 18 of the rotary link 14, thereby unlocking the trigger 8. When the trigger 8 is unlocked, because the loop 5 has caught the edge 415, the distal end of the tube 7 is substantially adjacent to the edge 415 of the tract 410, which is a desirable location for the deployment of the sealing element 160. The operator is then enabled to deploy the sealing element 160.

Even though a spring loaded system is described above for locking and unlocking the trigger 8, one of ordinary skill in the art would appreciate that any locking mechanism may be employed in accordance with an embodiment of the present invention, such as a hydraulic and/or electronic system.

In addition to locking and unlocking the trigger 8, the indicator assembly 200 may also provide a visual and/or audio notification to the operator that the distal end of the tube 7 is in a desirable position. As will be explained in more detail with regard to FIGS. 4A, 4B, 5A, 5B, and 6, indicator 20 can be seen through indicator panel 13, which defines two windows 21, on the top plate 150 and indicates to the user when the appropriate time to press trigger 8 with rotary link 14 has been reached.

Figure 5A:
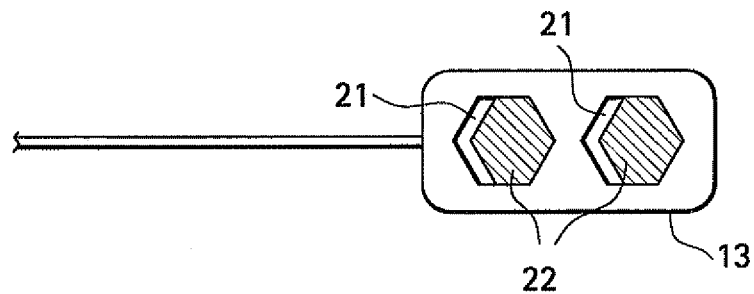
FIGS. 5(a-b) illustrate a top view of a window portion of the sealing element deployment device in accordance with a preferred embodiment of the present invention.
Figure 5B:
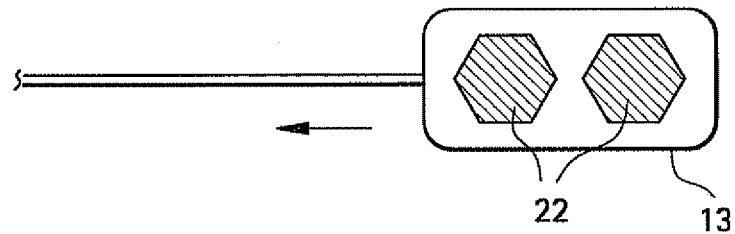

FIGS. 5A and 5B show a top view looking down through the windows 21, indicator 20 is provided with opaque portions 22. The windows 21 preferably have a shape consistent with the shape of markings 22 on the indicator 20. Thus, prior to the indicator wire 6 being axially displaced opposite of the housing 1 and/or tube 7, some or all of the windows 21 are clear, but when the indicator wire 6 is axially displaced opposite of the housing 1 and/or tube 7 as described above, markings 22 on the indicator 20 come into correspondence with the windows 21 of the indicator panel 13 as shown in FIG. 5B. When this registration occurs, trigger 8 may be pressed.

Figure 6:
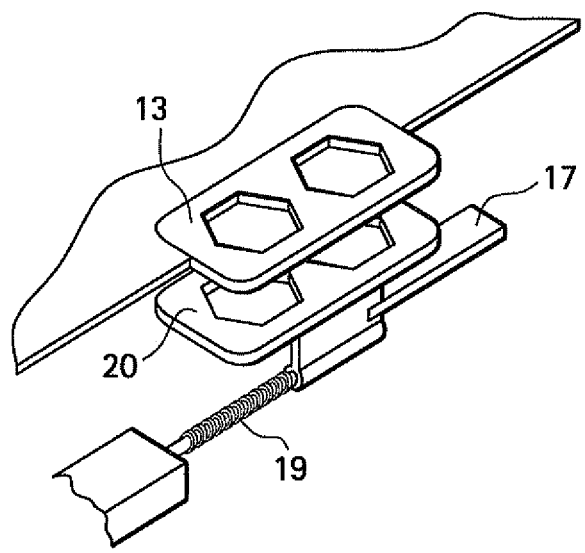
FIG. 6 illustrates a perspective view of a window portion of the sealing element deployment device in accordance with a preferred embodiment of the present invention.

FIG. 6 essentially shows the same thing as FIGS. 5A and 5B, but from a perspective view.

One of ordinary skill in the art would appreciate that though windows 21 are described, the indicator panel 21 may also utilize other mechanisms, such as electronic circuitry, light emitted diodes (LED), and/or other visual and/or audio mechanisms known in the art. For example, the device 100 may be configured such that when the indicator wire 6 engages the vessel wall 430 near the edge 415 of the tract 410, a circuit (not shown) is triggered within the housing 1 that causes a light to be emitted and/or an audio alarm to be invoked.

One of ordinary skill in the art would also appreciate that features of the anatomy of the patient's tissue can cooperate with the sealing element to facilitate the closure procedure. Preferably, the procedures of the invention position sealing element 160 so that structures located in the tissue between the patient's skin and the vessel wall 430 engage sealing element 160 and retain it against edge 415 of vessel wall 430.

For example, the transversalis fascia and the iliac fascia surround the femoral artery, forming the femoral sheath. In this region, the fasciae are relatively thick, fibrous and elastic membranes. As a result, penetration of the fasciae tend to involve a smaller puncture followed by the expansion of the hole in the fasciae to accommodate the size of the instrument forming the puncture. Upon withdrawal of the instrument, the elastic nature of the fasciae will tend to return the hole to a smaller size than the original puncture.

Figure 7:
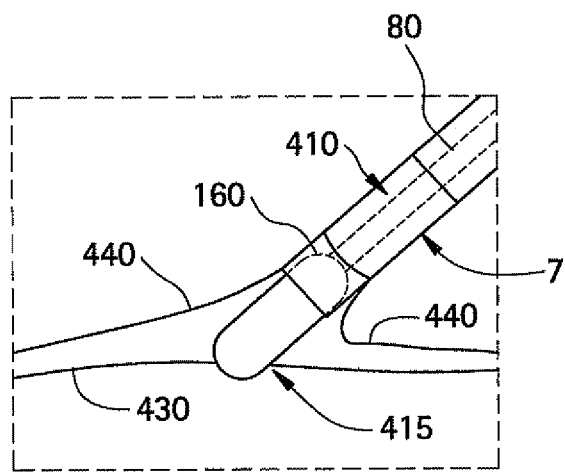
FIG. 7 illustrates a schematic view of the fascia being stretched away from the vessel wall by the deployment device in accordance with a preferred embodiment of the present invention.
Figure 8:
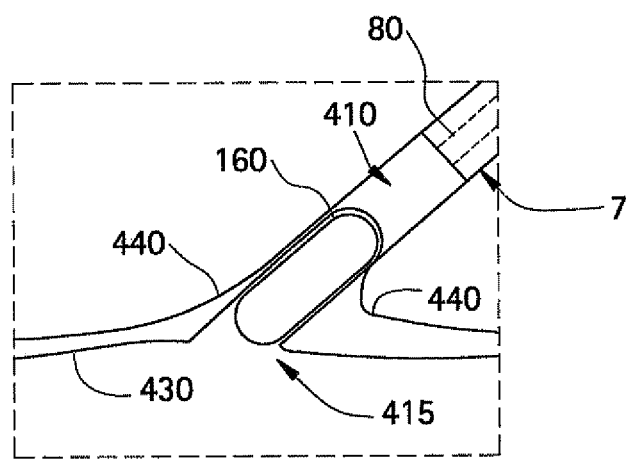
FIG. 8 illustrates a schematic view of the fascia retaining the sealing element against the vessel wall in accordance with a preferred embodiment of the present invention.
Figure 9:
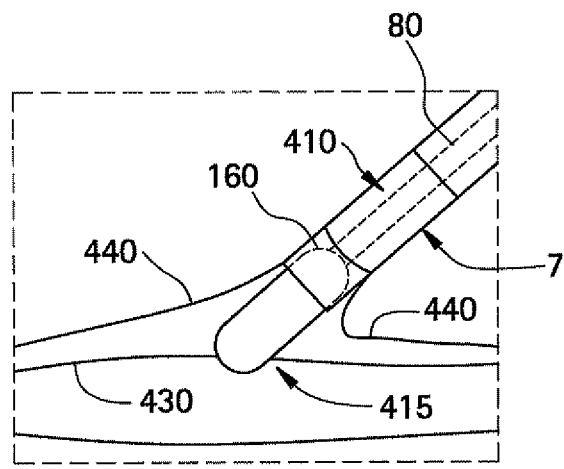
FIG. 9 illustrates another schematic view of the fascia retaining the sealing element against the vessel wall in accordance with a preferred embodiment of the present invention.

As can be seen in FIGS. 7-9, methods of the invention use these characteristics of the fasciae to help retain sealing element 150 against edge 415 of vessel wall 430. First, FIG. 7 shows an alternate detail of the operation described above with reference to FIGS. 2c and 2d. Introducer sheath 300 has been inserted through puncture wound 400, through fascia 440 and into lumen 420 of vessel 420. FIG. 7 shows the withdrawal of deployment tube 7 after sealing element 160 has been positioned adjacent edge 415 of blood vessel 430. Introducer sheath 300 has been withdrawn already, and now deployment tube 7 is being withdrawn to leave sealing element 160 in position. As shown in FIG. 7, the elastic nature of fascia 440 tends to close about deployment tube 7 so that as tube 7 is withdrawn, friction pulls fascia 440 away from vessel wall 430.

FIG. 8 shows that withdrawal of deployment tube 7 elastically displaces, or stretches, fascia 440 above sealing element 160, so that sealing element 160 is positioned between vessel wall 430 and fascia 440. When the range of travel of fascia 440 has been exceeded, fascia 440 pulls free from deployment tube and engages sealing element 160 has been placed adjacent edge 415 of vessel wall 430. Given the elastic nature of fascia 440, the size of the opening formed by introducer sheath 300 will have decreased so that the sheath cannot pass over sealing element 160. Further, the expandable nature of sealing element 160 described above will tend to prevent it from passing through an opening in the fascia 440. For example, a needle-punched PGA mat absorb some blood volume. Accordingly, as can be seen in FIG. 8, fascia 440 forms a "tent" over sealing element 160, holding it in position adjacent edge 415. The elasticity of fascia 440 transmits force to sealing element 160 to urge it against vessel wall 430 and effectively close lumen 420.

Alternatively, FIG. 9 shows another embodiment of the invention. Here, fascia 440 has pulled free from deployment tube 7 before sealing element 160 has been completely exposed. However, fascia 440 has still been stretched away from vessel wall 430 and will constrict about sealing element 160. The resulting friction of the tissue tract and the fascia retains the sealing element 160 in position adjacent edge 415 and urges sealing element 160 against vessel wall 430. The expandable nature of sealing element 160 increases its engagement with fascia 440.

Figure 10:
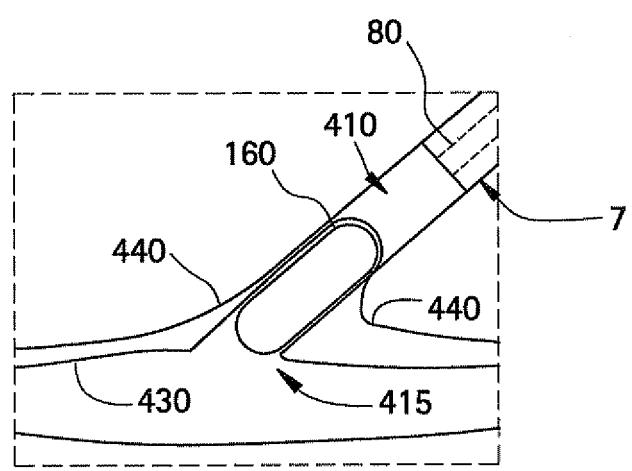
FIG. 10 illustrates another schematic view the fascia retaining the sealing element against the vessel wall in accordance with a preferred embodiment of the present invention.

FIG. 10 shows an alternative detail of the operation described above with reference to FIGS. 7 and 8. FIG. 10 shows that after the deployment tube 7 is withdrawn and the sealing element 160 is completely exposed, a portion of the sealing element 160 may be positioned in lumen 420 of vessel 430 and the remaining portion positioned within tract 410 of the wound 400. In other words, the sealing element may extend beyond edge 415 of vessel wall 430 and into the lumen 420. The fascia 440 can form a tent completely over sealing element 160 as shown in FIG. 8 or partially over sealing element 160 as shown in FIG. 9.

In addition to the interaction with the fascia 440, sealing element 160 is also stabilized and retained in position by other factors, including contraction of tissue above the tract.

Figure 11:
FIG. 11 is a photographic reproduction of a cross section of tissue showing the fascia retaining the sealing element against the vessel wall in accordance with a preferred embodiment of the present invention.

FIG. 11 is a photographic reproduction of a cross section of tissue showing placement of the sealing element. As can be seen, the sealing element is positioned between the fascia and the vessel wall. The elastic nature of the fascia helps retain the sealing element against the vessel wall and position it adjacent the puncture. FIG. 10 also shows that sealing element is preferably sized so that it can be positioned between the vessel wall and the fascia while maintaining the fascia in an elastically displaced position. Generally, the sealing element should be small enough to fit between the vessel wall and the elastically displaced fascia, yet large enough so that the elastically displaced fascia transmits force to the sealing element, holding it against the vessel wall.

The procedures of the invention have successfully been used to seal femoral arteriotomies. In one clinical study, average time to hemostasis using the inventive procedure averaged 138±42 sec, with patients undergoing diagnostic catheterization achieving hemostasis in 138±46 sec (45-296 sec) and patients undergoing percutaneous coronary interventions achieving hemostatis in 139±36 sec (36-245 sec) in 42 successful procedures. Notably, 83% of the patients achieved hemostasis by 2 min. Within the same study, average time to ambulation averaged 2.8 hours, with patients undergoing diagnostic catheterization ambulating in 2.78±1.23 hours (0.98-7.02 hours) and patients undergoing percutaneous coronary interventions ambulating in 2.93±1.22 hours (2.17-6.32 hours). In this study, 92% of the patients ambulated within 4 hours. The noted study experienced a 97% success rate (36/37) excluding roll-ins, where hemostasis was achieved within 5 min of plug delivery without closure-related serious adverse effects. Overall, 42 closures were achieved in 47 patients. In the study, no device-related serious adverse effects, including death, stroke, surgical repair, infection requiring hospitalization or bleeding requiring transfusion, were observed and one non-device related effect, a myocardial infarction occurred.

In the foregoing specification, the invention has been described with reference to specific embodiments thereof It will, however, be evident that various modifications and changes may be made thereto without departing from the broader spirit and scope of the invention. For example, preferred embodiments of the invention are directed to sealing femoral arteriotomies and reference is made to the fasciae surround the femoral artery, the femoral sheath. However, the invention can be applied to other lumens and membranes in the body as desired. Further, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

The invention claimed is:

1. An implantable medical device comprising:
a preformed, compressible, cylindrically shaped, porous fibrous structure configured for deployment in extravascular tissue to seal a passage through tissue communicating with a body lumen, the fibrous structure formed from at least one randomly oriented fiber comprising at least one polymer, the fibrous structure having a porosity ranging from 68% when the porous fibrous structure is in a compressed, pre-deployed configuration to 97% when the porous fibrous structure is in an uncompressed, deployed configuration.

2. The implantable medical device of claim 1 wherein the fibrous structure has a porosity ranging from 81 to 98%.

3. An implantable medical device comprising:
a preformed, compressible, cylindrically shaped, porous fibrous structure configured for deployment in extravascular tissue to seal a passage through tissue communicating with a body lumen, the fibrous structure formed from at least one randomly oriented fiber comprising at least one polymer, the fibrous structure having an absorbent capacity ranging from 2.75 g/g when the porous fibrous structure has a density of approximately 0.35 g/cc to 3.3 g/g when the porous fibrous structure has a density of approximately 0.45 g/cc.

4. An implantable medical device comprising:
a preformed, compressible, cylindrically shaped, porous fibrous structure configured for deployment in extravascular tissue to seal a passage through tissue communicating with a body lumen, the fibrous structure formed from at least one randomly oriented fiber comprising at least one polymer, the fibrous structure having a density ranging from 0.5 g/cc when the porous fibrous structure is in a compressed, pre-deployed configuration to 0.05 g/cc when the porous fibrous structure is in an uncompressed, deployed configuration.

5. The implantable medical device of claim 1, 3 or 4 wherein:
the randomly oriented fiber comprises at least one polymer with an absorption time varying from 30 to 90 days.

6. The implantable medical device of claim 1, 3, 4 or 5 wherein the fibrous structure is bioabsorbable.

7. The implantable medical device of claim 1, 3, 4 or 5 wherein the fibrous structure is non-woven and formed from crimped and stapled fibers.

* * * * *